United States Patent [19]
Harren et al.

[11] Patent Number: 6,036,721
[45] Date of Patent: Mar. 14, 2000

[54] PUNCTURE CLOSURE

[75] Inventors: Ernst-Diethelm Harren, Würselen; Christian Bangert, Aachen, both of Germany

[73] Assignee: CAP Incorporated, Panama City, Panama

[21] Appl. No.: 09/313,337

[22] Filed: May 17, 1999

Related U.S. Application Data

[63] Continuation of application No. PCT/DE97/02684, Nov. 17, 1997.

[30] Foreign Application Priority Data

Nov. 16, 1996 [DE] Germany .......................... 196 47 496
Jun. 21, 1997 [DE] Germany .......................... 197 26 386

[51] Int. Cl.[7] .................................................. A61B 17/04
[52] U.S. Cl. ........................................................... 606/213
[58] Field of Search ................................. 606/213, 214, 606/215

[56] References Cited

U.S. PATENT DOCUMENTS 3,310,051  3/1967  Schulte ................................. 604/175
5,234,459  8/1993  Lee ....................................... 606/203

FOREIGN PATENT DOCUMENTS

| 134745 | 3/1985 | European Pat. Off. . |
| 4429230 | 8/1994 | Germany . |
| 4418910 | 7/1995 | Germany . |
| 9504511 | 2/1995 | WIPO . |
| 9605774 | 2/1996 | WIPO . |

*Primary Examiner*—Gary Jackson
*Attorney, Agent, or Firm*—Thomas R. Vigil

[57] ABSTRACT

The present invention relates to a puncture seal for sealing a blood vessel having a puncture opening in a body of a human being or an animal. The seal comprises a pressure chamber which can be attached to the body in the area of the puncture opening and subjected to an overpressure, wherein the pressure chamber has a supporting wall in an area opposite to the body. In order to create a puncture seal, in which the pressure chamber can be reliably sealed once the hypodermic needle has been removed, a sealing element made of a material with a certain elastic return force, which is at least 1 mm thick is provided and placed in the area of the support wall to be punctured by the hypodermic needle.

17 Claims, 2 Drawing Sheets

PUNCTURE CLOSURE

CROSS-REFERENCE TO RELATED APPLICATIONS

This application is a continuation of PCT Application No. PCT/DE 97/02684 filed Nov. 17, 1997 which claims priority from DE 196 47 496.5 filed Nov. 16, 1997 and DE 197 26 386.0 filed Jun. 21, 1997.

BACKGROUND OF THE INVENTION

1. Field of the Invention

The present invention relates to an arterial puncture closure for closing a punctured blood vessel in a human or animal body by means of his own blood. This puncture closure has a pressure chamber which can be loaded with excess pressure and which can be fastened onto the body in the vicinity of the puncture, whereas the part of the pressure chamber opposite the body is provided with a retaining wall.

2. Description of the Prior Art.

The DE-44 29 230, WO 96/05774 or the WO 97/06735 (published later) describe puncture closures for closing a punctured blood vessel. The pressure chamber of these puncture closures is filled with the blood running out of the blood vessel until the pressure in the pressure chamber equals the blood pressure in the blood vessel, so that a balance of pressure between the blood vessel and the pressure chamber is achieved. This balance of pressure stops the bleeding. The puncture closure disclosed in DE-44 29 230 or in WO 96/05774 has a nearly rigid retaining wall that is provided on their underside with an easily extensible pressure wall, preferably made of latex. Full reference is made to DE-44 29 230 and to WO 96/05774.

Before starting the therapeutic or diagnostic intervention the puncture closure is stuck onto the human or animal body in the area where the blood vessel will be punctured. Then, the cannula of the injection, the catheter or the like is pierced through the pressure chamber, particularly through the retaining wall and through the pressure wall, before it pierces the skin and the tissue of the patient to reach the blood vessel aimed at. Now, the required therapeutic step may be taken.

In order to avoid the risk of punching out of the retaining wall particles of material when piercing it with the cannula, it has been suggested to provide the retaining and/or the pressure wall with preformed openings. This has not proved practicable, since the blood may run out of these preformed openings, weakening the adhesive layers of the puncture closure so that the blood may run out without control.

When the treatment is over, the cannula is taken out of the body of the patient and of the puncture closure, whereas the puncture closure keeps sticking on the body. Then, the opening in the retaining wall is closed by a closing bracket equipped with a glue and arranged on said retaining wall; see DE 44 29 230, WO 96/05774 or WO 97/06735. Single blood drops may hereby ooze out of the pressure chamber and/or of the cannula before the closing bracket has sealed the opening. These blood drops are unhygienic and represent a risk of infection for the caring staff. These blood drops are also weakening the glue so much that the closing bracket can no more be stuck in a pressure-sealed way onto the retaining wall.

SUMMARY OF THE INVENTION

The object of the present invention is therefore to provide a puncture closure whose pressure chamber may securely be closed once the cannula has been withdrawn.

The technical solution of this object according to the invention is to develop the puncture closure of the type mentioned above by providing it with a closing element of at least 1 mm thickness made of a material having an elastic restoring force. Said closing element is arranged in an area of the retaining wall in which the puncture by the cannula is planned, whereas the closing element is, preferably made at least partially of natural caoutchouc, synthetic caoutchouc, rubber, latex, silicone, liquid silicone, hydrogel, polymeric plastic or of a combination of at least some of the listed materials.

A puncture closure made according to this technical teaching has the advantage that the cannula is pushing the material with elastic restoring force apart or is displacing it, when entering the closing element, thereby, avoiding in a secure manner, the punching out of material particles. When pushing apart the material, the energy involved is stored in said material with elastic restoring force, so that the material is reintegrating its original position once the cannula has been withdrawn, thus closing again the opening made by the cannula's puncture (memory effect).

The material pushed apart by the cannula securely seals the place of puncture and protects it during the intervention against environmental influences since the material with the elastic restoring force is always sitting close to the cannula thanks to this restoring force.

In a preferred embodiment, the closing element is designed as a spherical segment or as a lens and is arranged, more particularly glued on the retaining wall, thereby advantageously reinforcing the retaining wall.

As already explained in DE 44 29 230 or WO 96/05774, an advantageous puncture closure has a retaining wall that may hardly be extended or that is rigid in order to prevent the pressure chamber from expanding away from the patient's body. This hardly extensible retaining wall brings the pressure chamber to expand mainly towards the body and that the tissue lying between the puncture closure and the blood vessel is compressed so that the blood cannot run into the tissue.

By reinforcing the retaining wall by means of a closing element according to the invention arranged on said retaining wall, it is possible to make the retaining wall, just like the pressure wall, of an extensible material. The actually extensible retaining wall is indeed getting so inflexible by the closing element fastened onto it that the pressure chamber can no more expand significantly away from the body. The fact that the retaining wall and the pressure wall are made of the same extensible material has the advantage that the retaining wall and the pressure wall may be welded together in alignment or in surface so that a puncture closure manufactured according to this teaching may be produced at low cost and that the walls of the pressure chamber, joined together in a flow of material, are securely withstanding the blood pressure prevailing in the human and animal bodies.

A puncture closure with a retaining wall and a pressure wall of polyetherurethane having the same thickness and provided with a closing element arranged on the retaining wall has proved to have a sufficient extension towards the body when used under pressure. It may still be of advantage to make the retaining wall thicker than the pressure wall, since this measure further restrains the extension of the retaining wall.

The closing element may be covered by an outer layer being hardly extensible or rigid and preferably made of polyester or polyetherurethane. The advantage thereof is that the retaining wall will find it more difficult to extend away from the body, particularly when the outer layer is extending beyond the area assigned to the cannula puncture. The thus achieved sandwich-like structure of retaining wall—closure element—outer layer reliably prevents the retaining wall from extending too far away from the body.

Another advantage of the outer layer is that it protects the closing element against dirt and/or damage.

In a preferred embodiment, the outer layer is glued onto the particularly lens-shaped closing element with pressure or pretension so that the closure element is submitted to a certain pressure or pretension. The restoring effect of the material with elastic restoring force of which is made the closing element is reinforced by this measure since, due to the prevailing pressure alone, the closing element already aims at closing the puncture opening made by the cannula as soon as it is withdrawn from the puncture closure. In order to still reinforce this effect, the outer layer is advantageously made of a non or hardly extensible material as, for example of a polyester foil or of a foil, on a polyester basis. The pressure built up on the closing element is thus maintained.

The outer layer is extending until the edge of the puncture closure or even beyond. This has the advantage that the puncture closure may be easily seized with a finger since it has, thus as a whole, a palpable stability for the user. Another advantage thereof is that an adherent that is extending beyond the edge of the pressure chamber may be used to fasten the puncture closure on the patient's skin.

In a preferred embodiment the puncture closure is, at least partially and preferably in the area outside the pressure chamber, air permeable. Thus, the puncture closure stuck on the skin advantageously leaks sweat or other vapors so that no moisture is accumulating underneath the puncture closure that might attack the glue and so that the puncture closure does not inaccommodate the patient.

In a particularly preferred embodiment the retaining wall and the pressure wall are made of the same extensible material, whereas the retaining wall is thicker than the pressure wall. Due to the difference in thickness the retaining wall and the pressure wall have different capacities of extension. This difference in extension between the retaining wall and the pressure wall has proved to be sufficient to guide the forces occasioned by the pressure within the pressure chamber onto the tissue so that the puncture opening is closing. This is particularly true when the retaining wall and the pressure wall are made of an extensible polyetherurethane foil, a polyurethane foil or a polypropylene foil, whereas the retaining wall has a thickness of 30 μm up to 300 μm and the pressure wall a thickness of 5 μm to 100 μm. If the puncture closure is used for dialysis, the retaining wall has a thickness of preferably 40 μm and the pressure wall a thickness of preferably 25 μm. When used in cardiology, the retaining wall of the puncture closure has a thickness of preferably 100 μm and the pressure wall a thickness of preferably 60 μm. When polyetherurethane is used, no particles are punched out by the cannula that could get into the blood stream.

A retaining wall and a pressure wall made of polyetherurethane, polyether or polypropylene has also the advantage that these materials are air permeable and transparent, so that such a puncture closure is agreeable to wear on the skin and that the place of puncture on the patient's body remains visible, even when the puncture closure is stuck. This preferred puncture closure is, for example, used for hemodialysis on dialysis patients.

In an alternative embodiment of the puncture closure according to the invention the whole retaining wall is made of a material having an elastic restoring force, whereas the retaining wall either has a uniform thickness or is provided in the puncture area with a corresponding swelling. The pressure wall stuck on the underside of such a retaining wall is extensible as compared to the retaining wall.

It has to be seen to it that the material used for a retaining wall made of elastic material, as well as for the closing element, is thick enough so that the opening made by the cannula may be closed again. Corresponding tests with a closing element made of silicone showed that a material thickness of approximately 4 mm is sufficient to reliably close an opening made by a cannula of an outer diameter of 1,8 mm as they are used for hemodialysis. When using the puncture closure according to the invention in cardiology, far bigger opening diameters are made so that the thickness of material should advantageously be of up to 25 mm.

Since the blood pressure in the arteries is fluctuating between a peak value and a minimum value depending on the pulse (e.g. between two pulse beats), a certain amount of blood is running out of the pressure chamber as soon as the pressure in the artery is momentarily sinking due to the constant pressure built up in the pressure chamber. In order to avoid this, the pressure wall should advantageously be made of a layer having a thickness of 0,2 mm to 3 mm, preferably of 0,5 mm to 1 mm and being made of a material with elastic restoring force. Another possibility is to arrange inside the pressure chamber on the pressure wall a closing layer having a thickness of 0,2 mm to 3 mm, preferably of 0,5 mm to 1 mm and made of a material with elastic restoring force.

In both cases, the blood is running out of the blood vessel into the pressure chamber and first keeps the opening open, since the restoring force of the material is not big enough to completely close the opening. When a certain pressure has built up in the pressure chamber, the closing element or the pressure wall are partially compressed so that, together with the restoring force of the material, the opening in the pressure wall is now closed. The closing layer or pressure wall functioning as a one-way valve shortens the time needed for the pressure chamber to get filled so that, within a very short period of time, a higher maximum pressure may be achieved in the pressure chamber. These two features are improving the efficiency of the puncture closure according to the invention.

In another preferred embodiment the retaining wall is made of a material with elastic restoring force that is reinforced by fibers. These inelastic fibers may be long fibers arranged crosswise or they may constitute a net, for example.

The advantage thereof is that the retaining wall may be manufactured and more particularly cast together with the closure element made of caoutchouc, rubber, latex, hydrogel, (fluid) silicone, polymer plastic or the like so as to form one integral piece, but that, due to the unelastic fibers, is hardly extensible so that the pressure building up in the pressure chamber only causes the pressure wall to extend but not the retaining wall.

In still another preferred embodiment the retaining wall and the pressure wall are glued together with a silicone glue or with a synthetic caoutchouc. Retaining wall and pressure wall are particularly glued together when the retaining wall and the pressure wall are made of different materials. The problem hereby is that the glue layer is very much exposed to stripping due to the diac-like strain so that it is not able to provide a strong enough adhesive force. When using silicone glue or a synthetic caoutchouc, and more particularly when the glue layer is 0,1 mm to 1 mm thick, the line load is transmitted into a surface load via the thickness of the layer so that the glue may now much more easily control the occurring forces and keep together the two walls.

Since the bonding emulsion in the vicinity of the puncture opening only has a sealing function and no force, a bonding emulsion is applied in the central area of the pressure chamber of a preferred embodiment, said bonding emulsion having less adhesive strength than the other bonding emulsion. The central area of the pressure chamber may also be kept free of glue. This has the advantage that the puncture closure may be withdrawn more easily from the patient's body, without the closed puncture being strained by strong forces.

Further advantages of the puncture closure according to the invention will become clear in the description and in the drawing enclosed. The characteristics mentioned above and those mentioned below may be carried out according to the invention either individually or in any combination. The embodiments mentioned are only examples and are not limiting the scope of the invention. The drawing is showing embodiments as examples of a puncture closure according to the invention with the aid of which the invention will be explained in more details.

DESCRIPTION OF THE PREFERRED EMBODIMENT(S)

Figure 1:
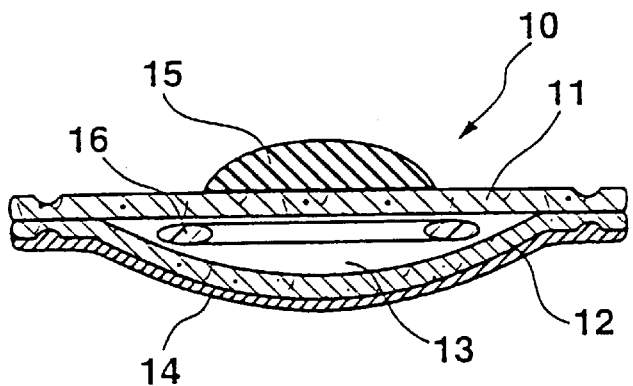
FIG. 1 shows a sectional side view of a puncture closure according to the invention with integrated drug carrier.

The different figures of the drawing show parts of the subject matter according to the invention in superproportional enlargements in order to better show its structure.

The four different embodiments shown in FIGS. 1 to 4 all have the same core structure, since all these puncture closures 10, 20, 30, 40 are provided with a retaining wall 11, 21, 31, 41 that is only a little bit extensible and that is made of a polyetherurethane foil of 40 μm thickness. Said retaining wall is welded in line or in surface with a pressure wall 12, 22, 32, 42 made of a polyetherurethane foil of 25 μm thickness so that a pressure chamber 13, 23, 33, 43 is provided between the retaining wall 11, 21, 31, 41 and the pressure wall 12, 22, 32, 42 that receives the blood running out of the blood vessel. The side of the puncture closure 10, 20, 30, 40 facing the body is provided with a skin-tolerated, biocompatible glue 14, 24, 34, 44 preferably on acrylate or silicone basis, by means of which the puncture closure 10, 20, 30, 40 may be fastened onto the patient's skin. In order for the glue layer to remain movable and operative it has to be provided with a protective foil that is not shown here.

A closing element 15, 25, 35, 45 is glued or vulcanized onto the retaining wall 11, 21, 31, 41, more particularly on its upper side, that means on the side of the puncture closure 10, 20, 30, 40 that is opposite the body. Said closing element 15, 25, 35, 45 is preferably arranged in the center on top of the corresponding pressure chamber 13, 23, 33, 43. This closing element 15, 25, 35, 45 is made of silicone and reinforces on one hand the retaining wall 11, 21, 31, 41 while it closes on the other the opening made by the insertion of the cannula (not shown) after said cannula has been withdrawn. In the embodiments shown in FIGS. 1 to 4 the closing element 15, 25, 35, 45 has the shape of a segment of a circle, that means that the lower side of the closing element 15, 25, 35, 45 is plane and that its upper side is bent. In other words, the closing element 15, 25, 35, 45 has the shape of a split lens.

This basic version of a puncture closure according to the invention has a retaining wall 11, 21, 31, 41 and a pressure wall 12, 22, 32, 42 made of the same material, but the retaining wall 11, 21, 31, 41 is thicker so that it is less extensible than the pressure wall 12, 22, 32, 42. This actually easy to extend polyetherurethane is reinforced in the area of the planned cannula insertion and beyond it by the spherical segment-shaped closing element 15, 25, 35, 45 made of silicone so that the retaining wall 11, 21, 31, 41 only extends a little when the pressure chamber 13, 23, 33, 43 is filled. Thus, the main expansion of the pressure chamber 13, 23, 33, 43 is occurring via the pressure wall 12, 22, 32, 42 in direction of the patient's body so that under no circumstances can the blood escape into the tissue, since said tissue is compressed.

By using similar materials for the pressure wall 12, 22, 32, 42 and for the retaining wall 11, 21, 31, 41, these two walls may easily be bonded together. Thus, a tight enough pressure chamber 13, 23, 33, 43 may be manufactured at low cost.

In the embodiment of the puncture closure 10 according to the invention and shown in FIG. 1 a drug carrier made of gauze or of a tissue matrix is integrated in the pressure wall 12. Said circular drug carrier 16 may be soaked with a hematostatic for a faster blood coagulation or with another drug.

Figure 2:
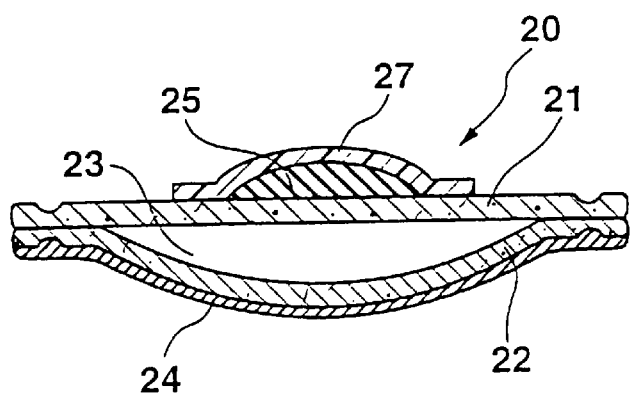
FIG. 2 shows a sectional side view of a puncture closure according to the invention with an outer layer.

In the embodiment shown in FIG. 2, the puncture closure 20 is provided on its upper side with an outer layer 27 made of a 40 pm thick polyester foil that completely covers the closing element 25. The outer layer 27 is sitting so close to the closing element 25 that said closing element is at least slightly compressed. The outer layer 27 is glued due to the gluing effect of the silicone of the closing element 25. This pressure exerted onto the closing element 25 is reinforcing the restoring force of the silicone, since now, additional exterior forces are acting onto the opening made by the cannula in order to close it. This effect is still reinforced by the fact that, when the pressure chamber 27 is filled, the closing element 25 on the retaining wall 21 is compressed tangentially to said retaining wall. Thus, the pressure exerted onto the closing element 25 to close the puncture is still further increased.

Figure 3:
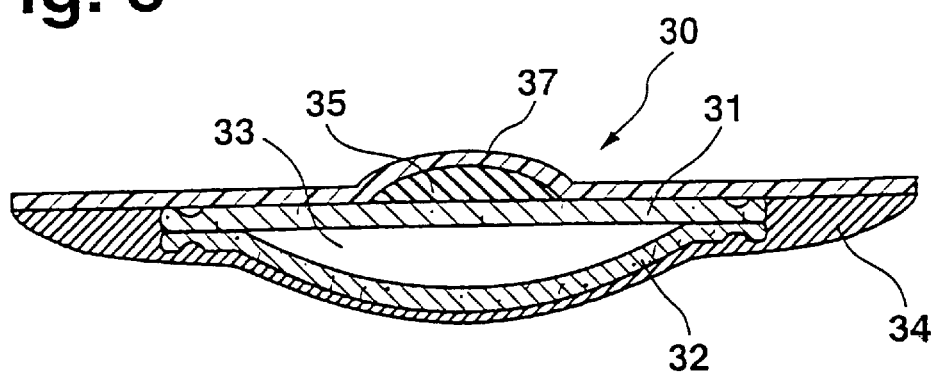
FIG. 3 shows a sectional side view of a puncture closure according to the invention with a lengthened outer layer.

In the embodiment shown in FIG. 3, the outer layer 37 is much bigger than the closing element 35 itself and extends beyond the edge of the retaining wall 31, so that the outer layer 37 is projecting clearly beyond the retaining wall 31. In the projecting area of the outer layer 37 a glue 34 is provided on the side facing the body so that the puncture closure 30 may reliably be fastened onto the patient's body.

Figure 4:
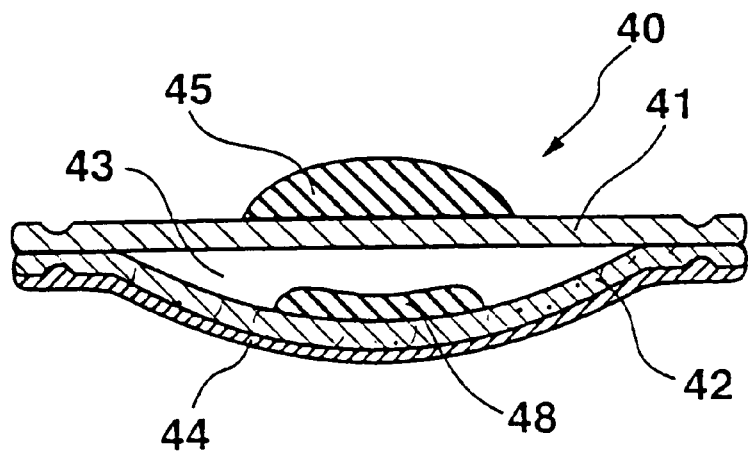
FIG. 4 shows a sectional side view of a puncture closure according to the invention with a closing layer integrated in the pressure chamber.

In the embodiment shown in FIG. 4, a closing layer 48 made of a material with an elastic restoring force, preferably of silicone, is integrated in the pressure chamber 43 of the puncture closure 40. Said closing layer 48 is located on the inner side of the pressure wall 42 and is arranged in the area in which the insertion of the cannula is planned. This closing layer 48 is acting like a one-way valve and hinders the blood from running out of the pressure chamber 43 during the momentary drop of pressure in the blood vessel.

Figure 5:
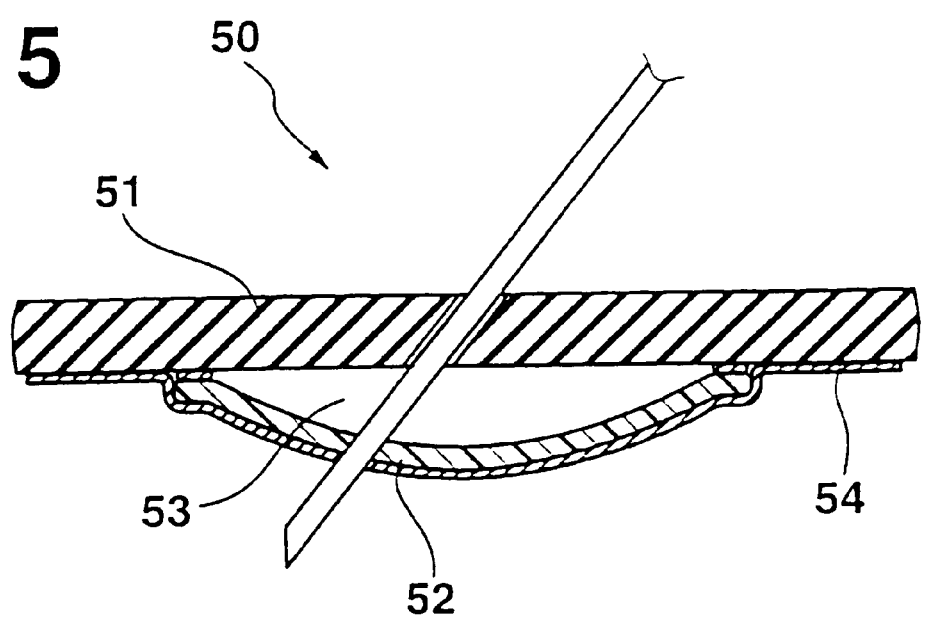
FIG. 5 shows a sectional side view of a puncture closure according to the invention with a closure element integrated in the retaining wall.

FIG. 5 shows an alternative embodiment of a puncture closure 50 according to the invention. Here, the retaining wall 51 is made of a thick layer of (natural) caoutchouc, latex or silicone. On its underside, an easily extensible pressure wall 52 is stuck that is made of a 25 μm thick polyetherurethane foil so that a pressure chamber 53 is provided between the retaining wall 51 and the pressure wall 52. In this embodiment too, the underside of the puncture closure 50 is coated with the above mentioned glue 54.

In an alternative embodiment, the outer layer may be made, just as the retaining wall, of (natural) caoutchouc, latex or silicone. As opposed to the retaining wall 51, the pressure wall 52 is then only given a thickness of 0,5 mm.

All puncture closures 10, 20, 30, 40, 50 described above are used for example in dialysis or in cardiology. When used in dialysis, the puncture closure according to the invention is inserted on the forearm in the area of the shunt, whereas in cardiology, the puncture closure according to the invention is inserted on the thigh in the area of the femoral artery. When used in dialysis, the cannulas regularly used have a diameter of 1,8 mm, so that a closing element having a thickness of 5 mm is sufficient to close the opening made by the cannula after completion of the intervention. In cardiology, the cannulas and/or catheters inserted into the blood vessel are much thicker and are reaching diameters of up to 5 mm, so that here, depending on the case, the closing element has to have a thickness of up to 25 mm in order to be able to reliably close the opening.

In an alternative, not shown embodiment, the puncture closure has a retaining wall and a pressure wall, both of them being made of a 150 μm thick polyetherurethane or incision foil. These two 150 μm thick foils may be bonded or vulcanized together several times or in surface, so that a strong connection between the foils is achieved. Said connection is so strong that it may withstand the pressure forces occurring in the pressure chamber when the puncture closure is used in cardiology.

All puncture closures 10, 20, 30, 40, 50 are transparent, in order to keep the blood vessel to be punctured at least approximately visible.

All the elements described in this application and made of a material with an elastic restoring force are at least partially made of rubber, natural caoutchouc, synthetic caoutchouc, latex, silicone, liquid silicone, hydrogel, polymer plastic or of a combination of some of the above mentioned materials.

We claim:

1. Arterial puncture closure for closing a punctured blood vessel in a human or animal body by means of his own blood, this puncture closure having a pressure chamber (13, 23, 33, 43, 53) which-can be loaded with excess pressure and which can be fastened onto the body in the vicinity of the puncture, whereas the part of the pressure chamber (13, 23, 33, 43, 53) opposite the body is provided with a retaining wall (11, 21, 31, 41, 51), said puncture closure comprises a closing element (15, 25, 35, 45) of at least 1 mm thickness made of a material having an elastic restoring force, said closing element (15, 25, 35, 45) is arranged in an area of the retaining wall (11, 21, 31, 41, 51) in which the puncture by the cannula is planned.

2. Puncture closure according to claim 1,
wherein the closing element (15, 25, 35, 45) is made of a material having an elastic restoring force, whereas the closing element (15, 25, 35, 45) is selected from a group consisting of at least partially made from a material consisting essentially of natural caoutchouc, synthetic caoutchouc, rubber, latex, silicone, liquid silicone, hydrogel, polymeric plastic or a combination thereof.

3. Puncture closure according to claim 1,
wherein the closing element (15, 25, 35, 45) is arranged, on the retaining wall (11, 21, 31, 41).

4. Puncture closure according to claim 1,
wherein the closing element (15, 25, 35, 45) is designed as a spherical segment.

5. Puncture closure according to claim 1,
wherein an outer layer (27, 37, 47) is arranged on the closing element (15, 25, 35, 45), whereas said outer layer (27, 37, 47) is made of one of polyester or polyetherurethane, which is substantially or rigid and which have a thickness of between 10 μm and 100 μm.

6. Puncture closure according to claim 5,
wherein the outer layer (27, 37, 47) is extending beyond the area in which the puncture by the cannula is planned.

7. Puncture closure according to claim 5,
wherein the outer layer (27, 37, 47) is fastened on the puncture closure (20, 30, 40) in such a way that the closing element (25, 35, 45) is constantly under pressure or pretension.

8. Puncture closure according to claim 1,
wherein the pressure chamber (13, 23, 33, 43, 53) is provided, in its area facing the puncture opening, with an extensible pressure wall (12, 22, 32, 42, 52).

9. Puncture closure according to claim 8,
wherein the retaining wall (11, 21, 31, 41) as well as the pressure wall (12, 22, 32, 42) are made of the same extensible material.

10. Puncture closure according to claim 9,
wherein the retaining wall (11, 21, 31, 41, 51) is thicker than the pressure wall (12, 22, 32, 42, 52).

11. Puncture closure according to claim 9,
wherein the retaining wall (11, 21, 31, 41) is welded alignment with the pressure wall (12, 22, 32, 42) and is at least one of thermo-welded or ultrasonic welded.

12. Puncture closure according to claim 9,
wherein the retaining wall (11, 21, 31, 41) is made one of a foil of polyetherurethane, polyether or polypropylene having a thickness of between 30 μm and 100 μm, and that the pressure wall (12, 22, 32, 42) is made of a foil of polyetherurethane, polyether or polypropylene having a thickness of between 5 μm and 50 μm.

13. Puncture closure according to claim 8,
wherein a closing layer (48) made of a material with elastic restoring force and having a thickness of between 0.2 mm to 3 mm, is arranged on the inner side of the pressure wall (42) in the area in which the puncture by the cannula is planned.

14. Puncture closure according to claim 9,
wherein the retaining wall (51) is made of a layer of caoutchouc, latex or silicone having a thickness of between 1 mm and 25 mm and/or that the pressure wall is made of a layer of caoutchouc, latex or silicone having a thickness of between 0.2 mm and 3 mm.

15. Puncture closure according to claim 14,
wherein the retaining wall and/or the pressure wall are reinforced by fibers inserted in the material.

16. Puncture closure according to claim 1,
wherein the puncture closure is at least partially air breathable in at least the area outside the pressure chamber (13, 23, 43, 53).

17. Puncture closure according to claim 1,
wherein the puncture closure is transparent, at least in the area where the puncture by the cannula is planned in at least the whole area of the pressure chamber (13, 23, 33, 43, 53).

* * * * *